US008933238B2

(12) United States Patent
Bender et al.

(10) Patent No.: US 8,933,238 B2
(45) Date of Patent: Jan. 13, 2015

(54) ARYLOXY-PHTHALOCYANINES OF GROUP III METALS

(71) Applicant: Saudi Basic Industries Corporation, Riyadh (SA)

(72) Inventors: Timothy P. Bender, Toronto (CA); Benoit H. Lessard, Toronto (CA); Ahmed Abdelrahman, Toronto (CA); Amit Tevtia, Thuwal (SA)

(73) Assignee: Saudi Basic Industries Corporation, Riyadh (SA)

( * ) Notice: Subject to any disclaimer, the term of this patent is extended or adjusted under 35 U.S.C. 154(b) by 0 days.

(21) Appl. No.: 14/197,799

(22) Filed: Mar. 5, 2014

(65) Prior Publication Data

US 2014/0256954 A1 Sep. 11, 2014

Related U.S. Application Data

(60) Provisional application No. 61/776,215, filed on Mar. 11, 2013.

(51) Int. Cl.
*C07F 5/06* (2006.01)
*C07F 5/00* (2006.01)
*H01L 51/00* (2006.01)
*H01L 51/42* (2006.01)

(52) U.S. Cl.
CPC .............. *C07F 5/069* (2013.01); *C07F 5/003* (2013.01); *H01L 51/0078* (2013.01); *H01L 51/0081* (2013.01); *H01L 51/0082* (2013.01); *H01L 51/4253* (2013.01)
USPC ........................................ 548/108

(58) Field of Classification Search
CPC ..................................... C07F 5/0699
USPC ........................................ 548/108
See application file for complete search history.

(56) References Cited

U.S. PATENT DOCUMENTS

| 3,509,146 A | 4/1970 | Brach et al. ............... 540/121 |
| 4,125,414 A | 11/1978 | Tang et al. ............... 136/263 |
| 4,175,981 A | 11/1979 | Loutfy et al. ............... 136/255 |
| 4,461,922 A | 7/1984 | Gay et al. ............... 136/249 |
| 6,198,091 B1 | 3/2001 | Forrest et al. ............... 250/214.1 |
| 6,198,092 B1 | 3/2001 | Bulovic et al. ............... 250/214.1 |
| 6,451,415 B1 | 9/2002 | Forrest et al. ............... 428/212 |
| 7,056,632 B2 | 6/2006 | Ioannidis ............... 430/56 |
| 7,232,617 B2 | 6/2007 | Lee et al. ............... 428/690 |
| 7,291,782 B2 | 11/2007 | Sager et al. ............... 136/250 |
| 7,329,709 B2 | 2/2008 | Gaudiana et al. ............... 525/403 |
| 7,419,846 B2 | 9/2008 | Shtein ............... 438/82 |
| 7,435,617 B2 | 10/2008 | Shtein ............... 438/99 |
| 7,462,711 B2 | 12/2008 | Takaki et al. ............... 540/139 |
| 7,462,774 B2 | 12/2008 | Roscheisen et al. ............... 136/256 |
| 7,592,539 B2 | 9/2009 | Peumans et al. ............... 136/263 |
| 7,605,327 B2 | 10/2009 | Roscheisen et al. ............... 136/263 |
| 7,645,934 B1 | 1/2010 | Fidanza et al. ............... 136/263 |
| 7,675,057 B2 | 3/2010 | Drechsel et al. ............... 257/40 |
| 7,686,978 B2 | 3/2010 | Petrov et al. ............... 252/301.16 |
| 7,713,779 B2 | 5/2010 | Firon et al. ............... 438/99 |
| 7,767,112 B2 | 8/2010 | Hou et al. ............... 252/500 |
| 7,781,759 B2 | 8/2010 | Song et al. ............... 257/40 |
| 7,868,536 B2 | 1/2011 | Aurongzeb ............... 313/503 |
| 7,955,889 B1 | 6/2011 | Yang et al. ............... 438/82 |
| 8,017,863 B2 | 9/2011 | Forrest et al. ............... 136/263 |
| 8,057,870 B2 | 11/2011 | Lee et al. ............... 428/1.33 |
| 8,114,704 B2 | 2/2012 | Kim et al. ............... 438/99 |
| 8,115,378 B2 | 2/2012 | Ionkin ............... 313/504 |
| 8,134,145 B2 | 3/2012 | Lee et al. ............... 257/40 |
| 8,179,589 B2 | 5/2012 | Wu et al. ............... 359/296 |
| 2005/0098726 A1 | 5/2005 | Peumans et al. ............... 250/338.1 |
| 2005/0224905 A1 | 10/2005 | Forrest et al. ............... 257/461 |
| 2005/0227406 A1 | 10/2005 | Shtein et al. ............... 438/99 |
| 2006/0005877 A1 | 1/2006 | Spivack et al. ............... 136/263 |
| 2006/0174934 A1 | 8/2006 | Sager et al. ............... 136/256 |
| 2006/0272701 A1 | 12/2006 | Ajayan et al. ............... 136/263 |
| 2007/0090371 A1 | 4/2007 | Drechsel et al. ............... 257/79 |
| 2007/0137701 A1 | 6/2007 | Sainte Catherine et al. .. 136/263 |
| 2007/0225491 A1 | 9/2007 | De Cupere et al. ............... 540/141 |
| 2007/0290195 A1 | 12/2007 | Forrest ............... 257/40 |
| 2008/0299382 A1 | 12/2008 | Moon et al. ............... 428/323 |
| 2009/0044864 A1 | 2/2009 | Thompson et al. ............... 136/263 |
| 2009/0173372 A1 | 7/2009 | Carroll et al. ............... 136/244 |
| 2009/0251765 A1 | 10/2009 | Miteva et al. ............... 359/326 |
| 2009/0266418 A1 | 10/2009 | Hu et al. ............... 136/260 |
| 2011/0168984 A1 | 7/2011 | Forrest et al. ............... 257/40 |
| 2012/0068123 A1 | 3/2012 | Sundarraj et al. ............... 252/506 |
| 2012/0132898 A1 | 5/2012 | Pan et al. ............... 257/40 |

FOREIGN PATENT DOCUMENTS

CN 1 583 762 2/2005
CN 101872842 10/2010
(Continued)

OTHER PUBLICATIONS

Soeda, et al. Document No. 152:538115, retrieved from CAPLUS, May 7, 2010.*
Om, et al. Document No. 150:331527, retrieved from CAPLUS, Jan. 7, 2008.*
Liu, et al. Document No. 151:19377, retrieved from CAPLUS, Dec. 17, 2007.*
Huang, et al. Document No. 143:487843, retrieved from CAPLUS, Nov. 9, 2005.*
Escano, et al. Document No. 136:233689, retrieved from CAPLUS, Mar. 15, 2002.*
Krutak, et al. Document No. 127:301311, retrieved from CAPLUS, Sep. 27, 1997.*

(Continued)

*Primary Examiner* — Shawquia Jackson
(74) *Attorney, Agent, or Firm* — Fulbright & Jaworski LLP

(57) ABSTRACT

The present disclosure relates to a compound comprising an aryloxy-phthalocyanine compound of Group III metals, a method for preparing the aryloxy-phthalocyanine compound of Group III metals and an article of manufacture made therefrom.

20 Claims, 1 Drawing Sheet

(56) References Cited

FOREIGN PATENT DOCUMENTS

| | | |
|---|---|---|
| DE | 10 2005 031974 | 1/2007 |
| DE | 102006023075 | 12/2007 |
| EP | 1722424 | 11/2006 |
| EP | 2 644 660 | 10/2013 |
| JP | 57091565 | 6/1982 |
| JP | 60201672 | 10/1985 |
| JP | 63010909 | 3/1988 |
| JP | 63060367 | 11/1988 |
| JP | 04-360150 | 12/1992 |
| JP | 02678830 | 11/1997 |
| JP | 03395949 | 4/2003 |
| JP | 2003-152208 | 5/2003 |
| JP | 2007-027566 | 2/2007 |
| JP | 2007-073619 | 3/2007 |
| JP | 2009-193763 | 8/2009 |
| JP | 04430862 | 3/2010 |
| JP | 2010-101987 | 5/2010 |
| JP | 2011-155185 | 8/2011 |
| JP | 2012-028607 | 2/2012 |
| JP | 2012-092229 | 5/2012 |
| KR | 2009-042881 | 5/2009 |
| KR | 2012-054643 | 9/2010 |
| WO | WO 02/20639 | 3/2002 |
| WO | WO 2011-030117 | 3/2011 |
| WO | WO 2011-041407 | 4/2011 |
| WO | WO 2012-058788 | 5/2012 |

OTHER PUBLICATIONS

Kraus, et al. Document No. 125:264328, retrieved from CAPLUS, Sep. 3, 1996.*

Krutak, et al. Document No. 123:145721, retrieved from CAPLUS, Jun. 8, 1995.*

International Search Report and Written Opinion issued in PCT/IB2014/000911, dated Jul. 24, 2014.

Zhu, R-Y et al. "Ultrafast dynamics of the excitons in a series of axially and bridged substituted phthalocyanine thin films." Chemical Physics Letters, Elsevier BV, NL, vol. 398, No. 4-6, pp. 308-312. 2004.

Chen, Y. et al. "Photophysical studies on axially substituted indium and gallium phthalocyanines upon UV-Vis laser irradiation." Solid State Communications, Pergamon, GB, vol. 131, No. 12, pp. 773-778. 2004.

Liu et al. "Optical limiting properties of axially substituted indium phthalocyanines in the solid PMMA composite films." Materials Chemistry and Physics, Elsevier SA, Switzerland, Taiwan, Republic of China, vol. 107, No. 2-3, pp. 189-192. 2007.

Kraus, G. A. et al. "A Convenient Method for Connecting Aluminum Phthalocyanine to Phenols via the Al-0 Bond." Synlett, pp. 726. 1996. URL: https://www.thieme-connect.de/products/ejournals/pdf/10.1055/s-1996-5531.pdf.

Owen, J. E. et al. "Phthalocyaninoaluminum compounds." Inorganic Chemistry, vol. 1, No. 2, pp. 332. 1962.

Maree, Suzanne Elizabeth. (2001). *Effects of Axial Ligands on the Photosensitising Properties of Silicon Octaphenoxyphthalocyanines* (Doctoral Dissertation). Rhodes University, Grahamstown, South Africa.

Maree, Michiel David. (2001). *Effects of Axial Ligands on the Photosensitising Properties of Silicon Octaphenoxyphthalocyanines* (Doctoral Dissertation). Rhodes University, Grahamstown, South Africa.

Chauke, Vongani Portia. (2008). *Synthesis, Photochemical and Photophysical Properties of Gallium and Indium Phthalocyanine Derivatives*. (Doctoral Dissertation). Rhodes University, Grahamstown, South Africa.

Amao, Y., & Komori, T. (2003). Dye-Sensitized Solar Cell Using a TiO2 Nanocrystalline Film Electrode Modified by an Aluminum Phthalocyanine and Myristic Acid Coadsorption Layer. *Langmuir*, 19, 8872-8875.

Durmus et al. (2007). Synthesis, photophysical and photochemical properties of aryloxy tetra-substituted gallium and indium phthalocyanine derivatives. *Tetrahedron*, 63, 6, 1385-1394.

C.W. Tang. (1986). Two-layer organic photovoltaic cell. *Appl. Phys. Lett.*, 48(2), 183-185.

N. Karl et al. (1994). Efficient Organic Photovoltaic Cells. The Role of Excitonic Light Collection, Exciton Diffusion to Interfaces, Internal Fields for Charge Separation, and High Charge Carrier Mobilities. *Mol. Cryst. Liq. Cryst.*, 252, 243-258.

M.V. Martinez-diaz, et al. (2010). Lighting porphyrins and phthalocyanines for molecular photovoltaics. *ChemChomm*, 46(38), 7090-7108.

C. J. Brabec et al. (2001). Plastic Solar Cells. *Advanced Functional Materials*, 11(1), 15-26.

J. Xue et al. (2005). Mixed donor-acceptor molecular heterojunctions for photovoltaic applications. II. Device performance. *Journal of Applied Physics*, 98(12), 124903.

J. Drechsel et al. (2004). MIP-type organic solar cells incorporating phtalocyanine/fullerene mixed layers and doped widegap transport layers. *Org. Electron.*, 5(4), 175.

Maennig et al. (2004). Organic p-i-n solar cells. *Applied Physics A*, 79(1), 1-14.

P. Peumans et al. (2003). Small molecular weight organic thin-film photodetectors and solar cells. *Journal of Applied Physics*, 93(7), 3693-3723.

J. Drechsel et al. (2004). High efficiency organic solar cells based on single or multiple PIN structures. *Thin Solid Films*, 451-452, 515-517.

E. Brisson et al. (2011). Boron Subphthalocyanine Dyes: 3-Pentadecylphenol as a Solubilizing Molecular Fragment. *Ind. Eng. Chem. Res.*, 50(19), 10910-10917.

B. D'Andrade et al. (2005). Relationship Between the ionization and oxidation potentials of molecular organic semiconductors. *Organic Electronics*, 6(1), 11-20.

Leng, X. et al. "Axial Coordination of Porphyrinatocobalt(II) Complexes with Bis(pyridinolato)silicon(IV) Phthalocyanines." Eur. J. Inorg. Chem. vol. 2007, No. 29. 4615-4620. 2007.

Liu, J.-Y. et al. "Switching the photo-induced energy and electron-transfer processes in BODIPY-phthalocyanine conjugates." Chem. Commun. No. 12, 1517-1519. 2009.

Huang, J.-D. et al. "Photodynamic activities of a dicationic silicon(IV) phthalocyanine and its bovine serum albumin conjugates." Tetrahedron Letters, 44, 8029-8032. 2003.

Partial Search Report issued in PCT/IB2014/000984 dated Sep. 12, 2014.

* cited by examiner

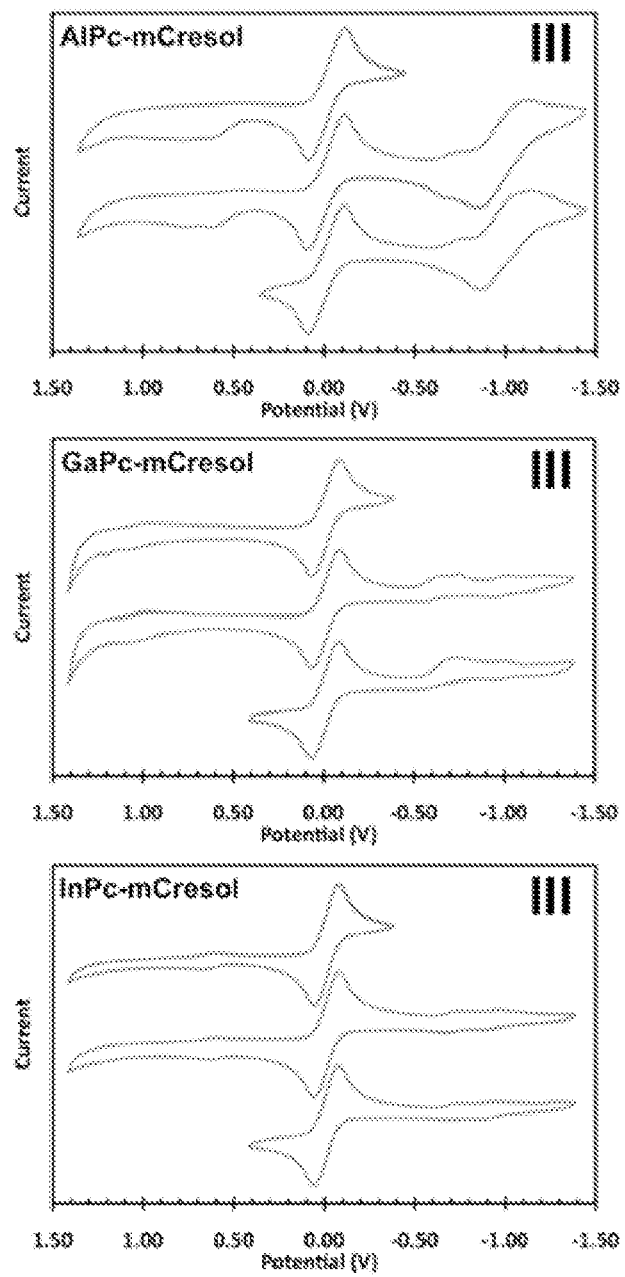

ARYLOXY-PHTHALOCYANINES OF GROUP III METALS

CROSS REFERENCE TO RELATED APPLICATIONS

This application claims the benefit of U.S. Provisional Application No. 61/776,215 filed Mar. 11, 2013. The contents of the referenced application(s) are incorporated into the present application by reference.

BACKGROUND OF THE INVENTION

A. Field of the Invention

The present disclosure relates to compositions comprising an aryloxy-phthalocyanine compound of a group III metal, methods for preparing said composition, and articles of manufacture made therefrom.

B. Description of Related Art

Organic materials can be used, for example, as semiconductors in low-cost photovoltaic cells. Organic materials can offer significant advantages in terms of materials and manufacturing cost relative to existing silicon technologies, and they do not typically suffer from supply demand pressures of the marketplace common to silicon. Current state of the art molecular based thin film devices can exhibit efficiencies similar to those of polymer based cells; however, organic thin film solar cells provide a significant advantage due to their ease of manufacture. Organic thin film solar cells do not necessarily utilize solution-processing methods employed for polymer-based cells. Instead, they typically use vacuum deposition methods that can be scalable and relatively cheap to implement. Such a device structure has the advantage that formation of a nano-phase separated bulk heterojunction film structure is not required.

Currently available organic semiconductors prepared using conventional methods generally suffer from low charge carrier mobility or electrical conduction. Additionally, in the case of small molecules, batch to batch variations are commonly observed in both film forming properties and electrical performance. It is therefore desirable to obtain new organic semiconducting materials having performance properties that can be tuned, optimized or engineered through molecular variation. These needs and other needs are satisfied by the compositions and methods of the present disclosure.

SUMMARY OF THE INVENTION

This invention relates generally to aryloxy-phthalocyaninene compounds, methods for preparing said compounds, and articles of manufacture made therefrom. In one aspect, the aryloxy-phthalocyanine compound comprises various aryloxy molecular fragments and group III metals.

Described herein is a compound of a general molecular structure (I):

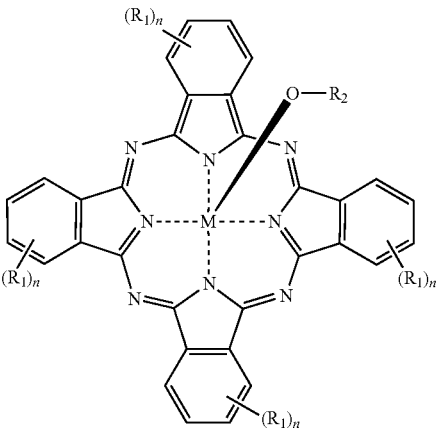

wherein M is chosen from the group III metals and comprises aluminum, gallium and indium; wherein "n" is an integer equal to or greater than 0; wherein each $R_1$ independently comprises a straight chain alkyl group, a branched alkyl group, a cycloalkyl group, an alkenyl group, an alkynyl group, an alkoxy group, an aryloxy group, heterocyclic group, a monocyclic aromatic group, a polycyclic aromatic group, an aryl group, an alkylaryl group, an arylalkyl group, an alkylene group, a hydrogen, a halogen, or a combination thereof; and wherein $R_2$ comprises an aryl containing group comprising from greater than or equal to about 6 to about 22 carbon atoms, wherein the aryl containing group can optionally be substituted at any one or more positions by one or more of heteroatoms, wherein the heteroatom, if present, can comprise a halogen, oxygen, sulfur, nitrogen, or a combination thereof.

In yet another aspect, described herein is a method for preparing a compound having the general structure (I), the method comprising: (a) providing a compound comprising a halogen-metal bond containing $R_1$ substituted phthalocyanines precursor, wherein the halogen comprises chloride, bromine, iodine, fluorine, or a combination thereof, and wherein each $R_1$ comprises a straight chain alkyl group, a branched alkyl group, a cycloalkyl group, an alkenyl group, an alkynyl group, an alkoxy group, an aryloxy group, heterocyclic group, a monocyclic aromatic group, a polycyclic aromatic group, an aryl group, an alkylaryl group, an arylalkyl group, an alkylene group, a hydrogen, a halogen, or a combination thereof; (b) providing a reactant comprising an optionally substituted aryl containing (—$R_2$) and/or optionally substituted arylalcohol containing groups (OH—$R_2$), wherein $R_2$ comprises from greater than or equal to about 6 to about 22 carbon atoms, wherein the reactant, if substituted, can be substituted at one or more positions by one or more heteroatoms comprising halogen, oxygen, sulfur, nitrogen, or a combination thereof; and (c) reacting the compound comprising a halogen-metal bond containing phthalocyanine precursor and the reactant in the presence of an organic solvent under conditions effective to form the compound of the general molecular structure (I), wherein the compound of the general molecular structure (I) is, in various aspects, non-soluble, negligibly soluble, partially soluble in an organic solvent, or at least partially soluble in an organic solvent.

In a further aspect, a photovoltaic cell is disclosed, wherein a photoactive region comprises a small molecule organic semiconductor comprising an aryloxy-phtalocyanine of a group III metal comprising a compound of a general formula (I):

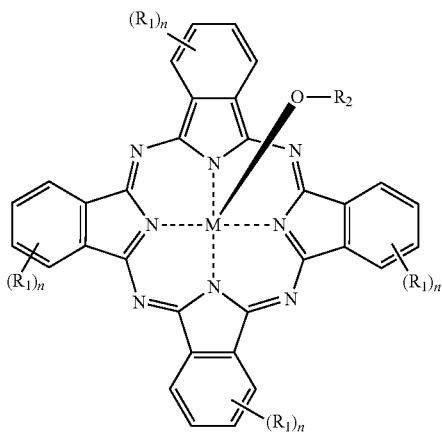

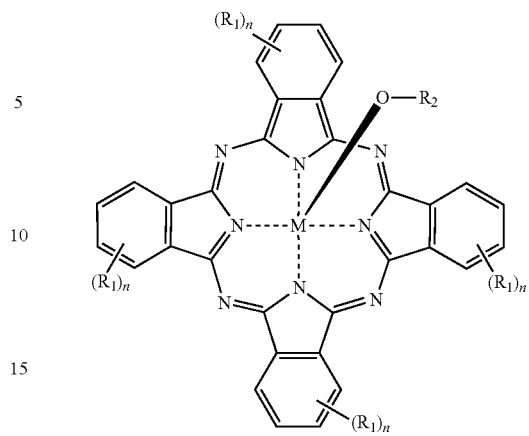

wherein M is one or more group III metals and comprises aluminum, gallium, indium, or a combination thereof; wherein "n" is an integer equal to or greater than 0; wherein each $R_1$ independently comprises a straight chain alkyl group, a branched alkyl group, a cycloalkyl group, an alkenyl group, an alkynyl group, an alkoxy group, an aryloxy group, heterocyclic group, a monocyclic aromatic group, a polycyclic aromatic group, an aryl group, an alkylaryl group, an arylalkyl group, an alkylene group, a hydrogen, a halogen, or a combination thereof; and wherein $R_2$ comprises an aryl containing group comprising from greater than or equal to about 6 to about 22 carbon atoms, wherein the aryl containing group can optionally be substituted at any one or more positions by one or more of heteroatoms, wherein the heteroatom, if present, can comprise a halogen, oxygen, sulfur, nitrogen, or a combination thereof.

In yet another aspect, methods for preparing a photovoltaic device and/or cell comprising an aryloxy-phthalocyanine of a group III metal are also disclosed.

Additional advantages will be set forth in part in the description which follows, and in part will be obvious from the description, or can be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below. Like numbers represent the same elements throughout the figures.

FIG. 1 illustrates cyclic voltammograms of m-cresol-AlPc, m-cresol-GaPc and m-cresol-InPc, in accordance with various aspects of the present disclosure.

DETAILED DESCRIPTION OF THE INVENTION

In one aspect, described herein are compounds of a general structure (I):

wherein M comprises aluminum, gallium, indium, or a combination thereof; wherein "n" is an integer equal to or greater than 0; wherein each $R_1$ comprises a straight chain alkyl group, a branched alkyl group, a cycloalkyl group, an alkenyl group, an alkynyl group, an alkoxy group, an aryloxy group, heterocyclic group, a monocyclic aromatic group, a polycyclic aromatic group, an aryl group, an alkylaryl group, an arylalkyl group, an alkylene group, a hydrogen, a halogen, or a combination thereof and wherein $R_2$ comprises an optionally substituted aryl containing group comprising from greater than or equal to about 6 to about 22 carbon atoms, wherein the aryl containing group, if substituted, can be substituted at one or more positions by one or more of the same or different heteroatoms comprising a halogen, oxygen, sulfur, nitrogen, or a combination thereof.

In one aspect, "n" ranges from about 0 to about 4.

In another aspect, $R_2$ comprises an optionally substituted aryl containing group comprising from greater than or equal to about 6 to about 18 carbon atoms, or from greater than or equal to about 6 to about 10 carbon atoms and wherein not all of which are considered aromatic carbon atoms, wherein, the aryl containing group, if substituted, can be substituted at one or more positions by one or more of the same of different heteroatoms comprising a halogen, oxygen, sulfur, nitrogen, or a combination thereof.

In another aspect, $R_2$ does not comprise a metal.

In another aspect, $R_2$ does not comprise a heteroatom as a bridging group.

In other aspects, $R_1$ and $R_2$ can be the same or different and at least one of $R_1$ and $R_2$ can comprise a hydrocarbon, hydrogen or halogen such as, for example, bromine, chlorine, fluorine, or iodine, or a combination thereof.

In yet another aspect, $R_1$ and $R_2$ can be the same or different and at least one of $R_1$ and $R_2$ can comprise a $C_1$-$C_{20}$-alkyl group: straight-chain or branched hydrocarbon radicals having up to about 20 carbon atoms, for example $C_1$-$C_{10}$-alkyl or $C_{11}$-$C_{20}$-alkyl, or a $C_1$-$C_{10}$-alkyl, for example $C_1$-$C_3$-alkyl, such as methyl, ethyl, propyl, isopropyl, or $C_4$-$C_6$-alkyl, n-butyl, sec-butyl, tert-butyl, 1,1-dimethylethyl, pentyl, 2-methylbutyl, 1,1-dimethylpropyl, 1,2-dimethylpropyl, 2,2-dimethylpropyl, 1-ethylpropyl, hexyl, 2-methylpentyl, 3-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 2-ethylbutyl, 1,1,2-trimethylpropyl, 1,2,2-trimethylpropyl, 1-ethyl-1-methylpropyl, 1-ethyl-2-methylpropyl, or $C_7$-$C_{10}$-alkyl such as heptyl, octyl, 2-ethylhexyl, 2,4,4-trimethylpentyl, 1,1,3,3-tetramethylbutyl, nonyl or decyl, and/or isomers or combinations thereof.

In another aspect, $R_1$ and $R_2$ can be the same or different and at least one of $R_1$ and $R_2$ can comprise a $C_2$-$C_{20}$-alkenyl group: unsaturated, straight-chain or branched hydrocarbon radicals having from about 2 to about 20 carbon atoms and a double bond in any position, for example $C_2$-$C_{10}$-alkenyl or $C_{11}$-$C_{20}$-alkenyl, a $C_2$-$C_{10}$-alkenyl such as $C_2$-$C_4$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, or $C_5$-$C_6$-alkenyl, such as 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl or 1-ethyl-2-methyl-2-propenyl, and also $C_7$-$C_{10}$-alkenyl such as the isomers of heptenyl, octenyl, nonenyl, decenyl, or a combination thereof.

In yet another aspect, $R_1$ and $R_2$ can be the same or different and at least one of $R_1$ and $R_2$ can comprise a $C_2$-$C_{20}$-alkynyl group: straight-chain or branched hydrocarbon groups having from about 2 to about 20 carbon atoms and a triple bond in any position, for example $C_2$-$C_{10}$-alkynyl or $C_{11}$-$C_{20}$-alkynyl, a $C_2$-$C_{10}$-alkynyl such as $C_2$-$C_4$-alkynyl, such as ethynyl, 1-propynyl, 2-propynyl, 1-butynyl, 2-butynyl, 3-butynyl, 1-methyl-2-propenyl, or $C_5$-$C_7$-alkynyl, such as 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propenyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl or 1-ethyl-1-methyl-2-propynyl, and $C_7$-$C_{10}$-alkynyl such as the isomers of heptynyl, octynyl, nonenyl, decynyl, or a combination thereof.

In another aspect, $R_1$ and $R_2$ can be the same or different and at least one of $R_1$ and $R_2$ can comprise a $C_3$-$C_{18}$-Cycloalkyl group: monocyclic saturated hydrocarbon groups having from about 3 up to about 18 carbon ring members, or a $C_3$-$C_8$-cycloalkyl such as cyclopropyl, cyclobutyl, cyclopentyl, cyclohexyl, cycloheptyl or cyclooctyl, and a saturated or unsaturated cyclic system, for example norbornyl or norbenzyl. In yet another aspect, $R_1$ and/or $R_2$ can be substituted with groups independently selected from other isomers and enantiomers, including mixtures of isomers or enantiomers, that would one ordinary skill in the art would deem appropriate.

In another aspect, $R_1$ and $R_2$ can be the same or different and at least one of $R_1$ and $R_2$ can comprise a heterocycle, for example, five- to twelve-member, five- to nine-member, five- to six-member, ring systems having oxygen, nitrogen and/or sulfur atoms and optionally a plurality of rings, such as furyl, thiophenyl, pyrryl, pyridyl, indolyl, benzoxazolyl, dioxolyl, dioxyl, benzimidazolyl, benzthiazolyl, dimethylpyridyl, methylquinolyl, dimethylpyrryl, methoxyfuryl, dimethoxypyridyl, difluoropyridyl, methylthiophenyl, isopropylthiophenyl or tert-butylthiophenyl. Moreover, $R_1$ and/or $R_2$ can comprise a five- or six-member saturated nitrogen-containing ring systems attached via a ring nitrogen atom and which can comprise one or two further nitrogen atoms or a further oxygen or sulfur atom. In another aspect, $R_1$ and/or $R_2$ can be selected from $C_2$-$C_{17}$ heterocycloalkyl, for example, aziridinyl, oxiranyl, thiiranyl, azetidinyl, oxetanyl, thietanyl, pyrrolidinyl, tetrahydrofuranyl, tetrahydrothiophenyl, piperidinyl, tetrahydro-2H-pyranyl, tetrahydro-2H-thiopyranyl, azepanyl, oxepanyl, thiepanyl, azocanyl, oxocanyl, thiocanyl, imidazolidinyl, pyrazolidinyl, oxazolidinyl, piperazinyl, tetrahydropyrimidinyl, tetrahydropyridazinyl, oxazinanyl, morpholinyl, diazepanyl, thiomorpholinyl, and pyrrolo[3,4-c]pyrrolyl.

In one aspect, $R_1$ comprises a $C_1$-$C_{20}$-alkoxy group: a straight-chain or branched alkyl group having from about 1 to about 20 carbon atoms (as specified above) which is attached via an oxygen atom (—O—), for example $C_1$-$C_{10}$-alkoxy or $C_{11}$-$C_{20}$-alkoxy, a $C_1$-$C_{10}$-alkyloxy, or a $C_1$-$C_3$-alkoxy, for example methoxy, ethoxy, propoxy.

In another aspect, $R_1$ comprises an aryloxy containing group, for example, a mono- to tricyclic aromatic ring system (as described above) which is attached via an oxygen atom (—O—), or a mono- to bicyclic, or a monocyclic, aromatic ring system.

In another aspect, $R_1$ and $R_2$ can be the same or different and at least one of $R_1$ and $R_2$ can comprise an arylalkyl group, for example, a mono- to tricyclic aromatic ring system (as specified above) which is attached via a $C_1$-$C_{20}$-alkylene group, a mono- to bicyclic, or a monocyclic, aromatic ring system.

In another aspect, $R_1$ and/or $R_2$ comprise a $C_1$-$C_{20}$-alkylene group, for example, a straight-chain or branched hydrocarbon radicals having from about 1 to about 20 carbon atoms, for example $C_1$-$C_{10}$-alkylene or $C_{11}$-$C_{20}$-alkylene, $C_2$-$C_{10}$-alkylene, such as, for example, methylene, dimethylene, trimethylene, tetramethylene, pentamethylene or hexamethylene.

In another aspect, $R_1$ and/or $R_2$ comprise an aryl group, for example, a mono- to tricyclic aromatic ring system comprising from greater than or equal to about 6 to about 22 carbon ring members, for example phenyl, naphthyl or anthracenyl, a mono- to bicyclic, or a monocyclic, aromatic ring system.

In yet a further aspect, $R_2$ comprises a mono- to tricyclic aromatic ring system comprising from greater than or equal to about 6 to about 22 carbon ring members, greater than or equal to from about 6 and about 18 carbon ring members, or from greater than or equal to about 6 to about 10 carbon ring members, wherein not all carbons are necessarily aromatic, and wherein the ring system can optionally be substituted at any one or more positions by one or more heteroatoms. In another aspect, such a heteroatom, if present, can comprise a halogen, oxygen, sulfur, nitrogen, or a combination thereof. In a further aspect, a heteroatom is present and comprises a chlorine, fluorine, bromine, iodine, or a combination thereof.

In one aspect, $R_2$ comprises a mono- to tricyclic aromatic ring system comprising from greater than or equal to about 6 to about 22 carbon ring members, greater than or equal to about 6 and about 18 carbon ring members, or from greater than or equal to about 6 to about 10 carbon ring members, wherein not all carbons are necessarily aromatic, and wherein the ring system can optionally be substituted at any one or more positions by one or more halogens. In one aspect, the ring system can be substituted at all ring positions by one or more halogens. In another aspect, a halogen does not comprise chlorine. In another aspect, a halogen can comprise fluorine, chlorine, bromine, iodine, or a combination thereof. In a yet further aspect, wherein a single chlorine is present on a given ring system, the ring system is not substituted in a para-position. In a yet even further aspect, wherein a halogen comprises chlorine, the ring system is substituted at one or more ortho-positions. While not wishing to be bound to a particular theory, it is believed that the substituted $R_2$ can be highly electronegative to affect the electron cloud around the metal.

In another aspect, any of the hydrocarbon groups can be optionally substituted one, two, or more times at any position with the same or different substituting moiety such as nitrogen containing groups, for example, amino and/or nitro; a sulfur containing group, for example, thiol, sulfoxide, sulfate, and/or chlorosulfate; a hydroxyl group; a silicon containing group, for example, trisubstituted silane where the substituent is a hydrocarbon; a halogen, for example, bromine, chlorine, fluorine, and/or iodine; and/or a heteroatom moiety, having for example about 3 to about 15 atoms, and including an element selected, for example, from nitrogen, sulfur, silicon, and oxygen, such as thiophen-2-yl, thiophen-3-yl, pyridine-2-yl, pyridine-3-yl, pyridine-4-yl, furna-2-yl, furan-3-yl, and the like. Exemplary substituted hydrocarbon groups include, for example: 3-hydroxyhenan-1,6,-dyyl; 2-methyl-benzen-1, 4,-diyl; and 2,5-dimethylbenzene-1,4,diyl.

A. Synthetic Methods

Described herein are methods for making a compound having the general structure described herein. In one aspect, the method for preparing the compound described herein can comprise: (a) providing a compound comprising a halogen-metal bond containing $R_1$ substituted phthalocyanine precursor, wherein the halogen comprises chlorine, bromine, iodine, fluorine, or a combination thereof, and each $R_1$ comprises a straight chain alkyl group, a branched alkyl group, a cycloalkyl group, an alkenyl group, an alkynyl group, an alkoxy group, an aryloxy group, heterocyclic group, a monocyclic aromatic group, a polycyclic aromatic group, an aryl group, an alkylaryl group, an arylalkyl group, an alkylene group, a hydrogen, a halogen, or a combination thereof; (b) providing a reactant comprising an optionally substituted aryl (—$R_2$) and/or optionally-substituted arylalcohol group (OH—$R_2$), wherein $R_2$ comprises from greater than or equal to about 6 to about 22 carbon atoms, and wherein not all of the carbon atoms are necessarily aromatic, and if substituted, can be substituted at any one or more positions by one or more heteroatoms, such as, for example, a halogen, oxygen, sulfur, nitrogen, or a combination thereof, and (c) reacting the compound comprising a halogen-metal bond containing phthalocyanine precursor and the reactant in the presence of an organic solvent under conditions effective to form the compound of the general structure (I), wherein, in one aspect, the compound of the general structure (I) is non-soluble, negligibly soluble, partially soluble in an organic solvent, or at least partially soluble in an organic solvent.

The preparation of metal-free phthalocyanines (PC) is known in the art. For example, U.S. Pat. No. 3,509,146 describes the preparation of metal-free phthalocyanines (Pc) and related compounds by mixing 1,3-diiminoisoindolines or their heterocyclic analogs with alkylalanolamines. EP 0 373 643 A2 describes the preparation of metal containing phthalocyanines, for example, the synthesis of metal containing phthalocyanines by reaction of mixtures of o-phthalodinitriles and/or 1,30 diiminoisoindolines with metallic compounds. Furthermore, M. Durmus et al., Tetrahedron, 2007, 1385 describe preparation of halogen-metal bond containing phthalocyanines. These compounds can be prepared for example, by the treatment of phthalonitriles with a metal chloride in freshly distilled quinoline solvent.

In one aspect, step (b) of the method for preparing a compound having the general structure (I) comprises providing a reactant comprising an optionally substituted aryl (—$R_2$) and/or an optionally substituted arylalcohol groups (OH—$R_2$), wherein $R_2$ comprises from greater than or equal to about 6 to about 18 carbon atoms, or from greater than or equal to about 6 to about 10 carbon atoms, wherein not all of the carbon atoms are necessarily aromatic, and wherein, if substituted, the reactant can be substituted at one or more positions by one or more heteroatoms, for example, comprising a halogen, oxygen, sulfur, nitrogen, or a combination thereof.

In another aspect, step (b) of the method for preparing a compound having the general structure (I) comprises providing a reactant comprising an optionally substituted aryl (—$R_2$) and/or an optionally substituted arylalcohol groups (OH—$R_2$), wherein $R_2$ comprises a mono- to tricyclic aromatic ring system comprising from greater than or equal to about 6 to about 22 carbon ring members, greater than or equal to about 6 and about 18 carbon ring members, or from greater than or equal to about 6 to about 10 carbon ring members, wherein not all carbons are necessarily aromatic, and wherein the ring system can optionally be substituted at any one or more positions by one or more heteroatoms. In a further aspect, such a heteroatom, if present, can comprise a halogen, oxygen, sulfur, nitrogen, or a combination thereof. In a yet further aspect, a heteroatom, if present, can comprise a chlorine, fluorine, bromine, iodine, or a combination thereof.

In one aspect, step (b) of the method for preparing a compound having the general structure (I) comprises providing a reactant comprising an optionally substituted aryl (—$R_2$) and/or an optionally substituted arylalcohol groups (OH—$R_2$), wherein, $R_2$ comprises a mono- to tricyclic aromatic ring system comprising from greater than or equal to about 6 to about 22 carbon ring members, greater than or equal to about 6 and about 18 carbon ring members, or from greater than or equal to 6 to about 10 carbon ring members, wherein not all carbons are necessarily aromatic, and wherein the ring system can optionally be substituted at any one or more positions by one or more halogens. In one aspect, the ring system can be substituted at all ring positions by one or more halogens. In another aspect, a halogen does not comprise chlorine. In a further aspect, a halogen comprises fluorine, chlorine, bromine, iodine, or a combination thereof. In a yet further aspect, wherein a halogen comprises chlorine, the ring system is not substituted in a para-position. In a yet even further aspect, wherein a halogen comprises chlorine, the ring system is substituted at one or more ortho-positions. While not wishing to be bound to a particular theory, it is believed that the substituted $R_2$ cans to be highly electronegative to affect electron cloud around the metal.

In another aspect, the compound of the general structure (I) can be prepared in the presence of a solvent. In one aspect, a suitable solvent can comprise substances which are liquid at the temperatures of the process according to the invention and in which all compounds involved are at least partly soluble. For example, such solvents have boiling points of over about 100° C. at standard pressure (101.325 kPa). The solutions of the compounds of the general structure (I) used in the method according to the invention in the presence of a solvent can also have the properties of suspensions or dispersions. Suitable solvents can comprise, for example, aromatic compounds or polar aprotic compounds. In one aspect, the solvent can comprise toluene, xylene, mesitylene, teralin, chlorobenzene, dichlorobenzene, quinoline, pyridine, sulfolane, THF, chloromethane, chloroform, dimethyl sulfoxide, or a combination thereof. The amount of solvent which can be used in the process according to the invention is dependent upon the solubility of the compounds dissolved and can therefore vary within a wide range. In another aspect, one or more solvents can be added in excess (weight ratio).

In one aspect, the temperatures which are established for the preparation of the general compound of the structure (I) in the method according to the invention can vary within a wide range. In general, the selection of the temperature can, for example, depend on the solubility of one or more compounds involved to form the compounds of the of the general structure (I), and can be determined by one of ordinary skill in the art. In one aspect, wherein solubility is high, it can be possible, for example, to select relatively low temperatures for the reaction in the method according to the invention. The temperatures in the method according to the invention can generally be selected from the range of from about 0° C. to about 200° C. In another aspect, the temperature can be in the range of from about 20° C. to about 150° C. In another aspect, the temperature can be in the range of from about 70° C. to about 140° C.

In another aspect, the pressure range within which the method according to the invention for preparing the compound of the general structure (I) are performed can vary. In various aspects, the method according to the invention can be performed at standard pressure, slightly reduced pressure or else elevated pressure. In one aspect, the pressure can be selected from the range of from about 90 kPa to about 1000 kPa.

The process can be performed in any apparatus which is suitable for this purpose, such as, for example, those known to one skilled in the art of organic compounds. For the removal and workup of the compound of general molecular structure (I), it is possible to use any methods with which the person skilled in the art is familiar. For example, the removal can be performed by, for example, filtration or phase separation. In another aspect, the workup can comprise a purification step, such as, for example, washing the compounds with a liquid, and/or a drying step.

In another aspect, the duration of all time steps (a) to (c) overall, and also of any individual step, can vary, for example, depending on the temperature. In another aspect, the duration of all time steps together can vary within a wide range from a few minutes up to, for example, about 72 hours.

It should be understood that the methods described herein are intended to be exemplary and are not intended to be limiting. Other methods can be used to prepare the inventive compositions described herein, and the present invention is not intended to be limited to the specific methods recited herein.

B. Solar Cells

As used herein, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than HOMO energy level of the same material. A "higher" HOMO or LUMO energy level appears closer to the top of such a diagram than a "lower" HOMO or LUMO energy level.

In the context of organic materials, the terms "donor" and "acceptor" refer to relative positions of the HOMO and LUMO energy levels of two contacting but different organic materials. The term "electron donor" refers to the material's electron affinity. An electron donor material has a relative low electron affinity, i.e. the EA value has a smaller absolute value. As such, an electron donor material tends to act as p-type material. In other words, an electron donor material can act as a hole transport material. The term "electron acceptor" refers to material's electron affinity. An electron acceptor material has a relatively high electron affinity. As such, an electron acceptor material can act as an electron transport material.

The term "charge transport material" as used herein refers to a material transports charge, i.e. holes or electrons. An electron donor material transports holes and an electron acceptor material transports electrons.

The term "photoactive region" as used herein is a portion of a photosensitive device that absorbs electromagnetic radiation to generate excitation (i.e. electrically neutral excited state in form of electron-hole pairs).

Described herein is use of a compound having the general molecular structure (I). In one aspect, a photovoltaic cell comprising a compound having the general molecular structure (I) is described.

In one aspect, photovoltaic cell comprising a compound having the general molecular structure (I)

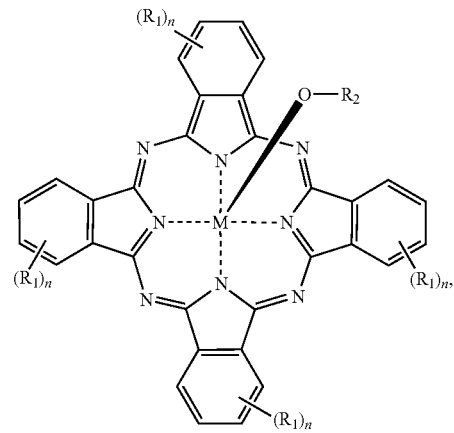

wherein M comprises aluminum, gallium, indium, or a combination thereof; wherein "n" is an integer equal to or greater than 0; wherein each $R_1$ can independently comprise a straight chain alkyl group, a branched alkyl group, a cycloalkyl group, an alkenyl group, an alkynyl group, an alkoxy group, an aryloxy group, heterocyclic group, a monocyclic aromatic group, a polycyclic aromatic group, an aryl group, an alkylaryl group, an arylalkyl group, an alkylene group, a hydrogen, a halogen, or a combination thereof;

wherein $R_2$ can comprise an optionally substituted aryl containing group comprising from greater than or equal to about 6 to about 22 carbon atoms, wherein the aryl containing group, if substituted, can be substituted at one or more positions with one or more of the same or different heteroatoms comprising a halogen, oxygen, sulfur, nitrogen, or a combination thereof.

In one aspect, no reports of phenoxy substituted group III metal containing phthalocyanines have been reported for the fabrication of organic photovoltaic devices.

Organic solar cells generally have a layered structure and generally comprise at least the following layers: anode, photoactive region, and cathode. These layers are generally disposed on a substrate. The structure of organic solar cells can vary, and various structures are known in the art, for example, in US 2005/0098726 and US 2005/0224905, which are fully incorporated here by reference.

Organic solar cells make use of heterogeneous junction regions of conjugated hole- and electron-conducting molecules to produce separated electrical charges after photo-induced charge transfer from the electron-donor to the electron-acceptor component.

In one aspect, the invention provides an organic solar cell comprising a substrate with at least one cathode, at least one anode, and at least one compound of the general molecular structure (I) as defined above as a photoactive material. In another aspect, the organic solar cell according to the invention comprises at least one photoactive region. A photoactive region can comprise two layers that each have a homogeneous composition and form a planar donor-acceptor heterojunction (PHJ) or a mixed layer forming a donor-acceptor bulk heterojunction (BHJ).

In organic semiconductors, light absorption can lead to the creation of excitations, (i.e. electron-hole pairs) through promotion of an electron from the HOMO to the LUMO level of the molecules. In order to produce separated charges, the excitations can be dissociated at the donor-acceptor interface, the driving force for this process being provided by the energy offset between the LUMO orbitals of the donor and acceptor molecules.

Consequently, the four basic steps occurring in a molecular based device: (a) light absorption/excitation generation; (b) excitation diffusion towards the donor-acceptor junction; (c) charge transfer/excitation dissociation; and (d) charge collection of the separated electrons and holes at the external electrodes.

The performance of photovoltaic cells is usually evaluated by analysis of the current-voltage (1-V) curves, from which key parameters such as the open-circuit ($V_{OC}$) (associated to the gap between the LUMO level of the acceptor and the HOMO level of the donor), short-circuit density ($J_{SC}$) (proportional to how much light can be absorbed), fill factor (FF) and power conversion efficiency (PCE) are extracted.

Suitable substrates for organic solar cells can comprise, for example, materials such as glass, ceramic, $SiO_2$, quartz, polymers such as polyvinyl chloride, polyolefins such as polyethylene and polypropylene, polyesters, fluoropolymers, polyamides, polyurethanes, polyalkyl(meth)acrylates, polystyrene and mixtures and composites thereof and combinations thereof.

Suitable electrodes (cathode and anode) can comprise metals (for example, of groups 8, 9, 10 or 11 of the Periodic Table, e.g. Pt, Au, Ag, Cu, Al, In, Mg, Ca), semiconductors (e.g. doped Si, doped Ge, indium tin oxide (ITO), gallium indium tin oxide (GITO), zinc indium tin oxide (ZITO), etc.), metal alloys (e.g. based on Pt, Au, Ag, Cu, etc., especially Mg/Ag alloys), semiconductor alloys, etc. One of the electrodes used can be a material essentially transparent to incident light. This includes, for example, ITO, doped ITO, FTO (fluorine doped tin oxide), AZO (aluminium doped ZnO), ZnO, $TiO_2$, Ag, Au, Pt. The other electrode used can be a material which essentially reflects the incident light. This includes, for example, metal films, for example of Al, Ag, Au, In, Mg, Mg/Al, Ca, etc.

For its part, the photoactive region can comprise at least one layer which comprises, as an organic semiconductor material, at least one compound of the general molecular structure (I) as defined above. In addition to the photoactive region, there can be one or more further layers. These include, for example, layers with electron-conducting properties (electron transport layer, ETL); layers which comprise a hole-conducting material (hole transport layer, HTL); exciton- and hole-blocking layers (e.g. EBLs) which should not absorb and multiplication layers. The role of the EBLs is to prevent damage of the acceptor layer due to cathode evaporation; eliminate undesired exciton quenching at the electron-acceptor/cathode interface; and provide a spacer between the photoactive region and reflecting cathode, thereby increasing the optical intensity at the donor-acceptor interface and, thus, the light absorption efficiency.

Suitable exciton- and hole-blocking layers are described, for example, in U.S. Pat. No. 6,451,415. Suitable materials for exciton blocker layers can, in various aspects, comprise, bathocuproin (BCP), 4,4',4"-tris[3-methylphenyl-N-phenylamino]triphenylamine (m-MTDATA) or polyethylenedioxy-thiophene (PEDOT).

In one aspect, a solar cell can comprise at least one photoactive donor-acceptor heterojunction. Upon optical excitation of an organic material, excitons are generated. For photocurrent to occur, the electron-hole pair has to be separated, typically at a donor-acceptor interface between two dissimilar contacting materials. At such an interface, the donor material forms a heterojunction with an acceptor material. If the charges do not separate, they can recombine in a geminate recombination process, also known as quenching, either radioactively, by the emission of light of a lower energy than the incident light, or non-radioactively, by the production of heat. Either of these outcomes is undesirable. In one aspect, when at least one compound of the general molecular structure (I) is used as the charge generating (donor) as well as HTM (hole transport material), and/or the corresponding electron accepting ETM (electron transport material) can be selected such that, after excitation of the compounds, a rapid electron transfer to the ETM takes place. Suitable ETMs are, for example, $C_{60}$ and other fullerenes, perylene-3,4;9,10-bis(dicarboximides) (PTCDIs), etc.

In one aspect, the heterojunction can have a planar configuration (PHJ) (cf. Two layer organic photovoltaic cell, C. W. Tang, Appl. Phys. Lett., 48 (2), 183-185 (1986) or N. Karl, A. Bauer, J. Holzapfel, J. Marktanner, M. Mobus, F. Stolzle, Mol. Cryst. Liq. Cryst., 252, 243-258 (1994), M. V. Martinez-diaz, G. de la Toree, T. Tones, ChemChomm., 7090-7108 (2010)).

In another aspect, the heterojunction can be implemented as a bulk heterojunction (BHJ) or interpenetrating donor-acceptor network. Organic photovoltaic cells with a bulk heterojunction are e.g. described by C. J. Brabec, N. S. Sariciftci, J. C. Hummelen in Adv. Funct. Mater., 11 (1), 15 (2001) or by J. Xue, B. P. Rand, S. Uchida and S. R. Forrest in J. Appl. Phys. 98, 124903 (2005), M. V. Martinez-diaz, G. de la Toree, T. Tones, ChemChomm., 7090-7108 (2010).

In another aspect, the compounds of the general molecular structure (I) can be used as a photoactive material in solar cells with M-i-M, p-i-n, p-n, M-i-p or M-i-n structure (M=metal, p=p-doped organic or inorganic semiconductor, n=n-doped organic or inorganic semiconductor, i=intrinsically conductive system of organic layers; cf., for example, J. Drechsel et al., Org. Electron., 5 (4), 175 (2004) or Maennig et al., Appl. Phys. A 79, 1-14 (2004)).

In another aspect, the compounds of the general molecular structure (I) can also be used as a photoactive material in tandem cells. Tandem cells comprise two combined unit cells, each one being a two-layer organic solar cell. Suitable tandem cells are described e.g. by P. Peumans, A. Yakimov, S. R. Forrest in J. Appl. Phys, 93 (7), 3693-3723 (2003) (cf. U.S. Pat. No. 4,461,922, U.S. Pat. No. 6,198,091 and U.S. Pat. No. 6,198,092) and are discussed in details below.

The compounds of the general molecular structure (I) can also be used as a photoactive material in tandem cells composed of two or more M-i-M, p-i-n, M-i-p or M-i-n diodes stacked on one another (cf. patent application DE 103 13 232.5) (J. Drechsel et al., Thin Solid Films, 451452, 515-517 (2004)).

In another aspect, the layer thicknesses of the M, n, i and p layers can range from about 10 to about 1,000 nm. Thin layers can be produced by vapor deposition under reduced pressure or in inert gas atmosphere, by laser ablation or by solution- or dispersion-processable methods such as spin-coating, knife-coating, casting methods, spraying, dip-coating or printing (e.g. inkjet, flexographic, offset, gravure; intaglio, nano-imprinting).

In order to improve efficiency of an organic solar cell, the average distance an exciton can diffuse from its generation to its dissociation site (donor-acceptor interface) can be reduced in an interpenetrating network of the donor and acceptor materials. In one aspect, the morphology of a bulk-heterojunction is characterized by a great donor-acceptor interface area and continuous carrier conducting pathways to the opposing electrodes.

Bulk heterojunctions can be produced by a gas phase deposition process (physical vapor deposition, PVD). Suitable methods are described in US 2005/0227406, to which reference is made here. To this end, typically a compound of general molecular structure (I) as electron donor and at least one electron acceptor material can be subjected to a vapor phase deposition by co-sublimation. PVD processes are performed under high-vacuum conditions and comprise the following steps: evaporation, transport, deposition.

In another aspect, other layers of solar cell can be produced by known methods, such as, for example, vapor deposition under reduced pressure or in inert gas atmosphere, by laser ablation or by solution- or dispersion-processable methods such as spin-coating, knife-coating, casting methods, spraying, dip-coating or printing (e.g. inkjet, flexographic, offset, gravure; intaglio, nano-imprinting). In another aspect, a complete solar cell can be produced by a gas phase deposition process.

In another aspect, the photoactive region (homogeneous layers or mixed layer) can be subjected to a thermal treatment directly after its preparation or after the preparation of other layers being part of the solar cell Annealing can improve the morphology of the photoactive region. In addition or alternatively to a thermal treatment, the photoactive region can be subjected to a treatment using a solvent-containing gas. In one aspect, saturated solvent vapors in air at ambient temperature are used. Suitable solvents can comprise toluene, xylene, chlorobenzene, trichloromethane, dichloromethane, N-methylpyrrolidone, N,N-dimethylformamide, ethyl acetate and mixtures thereof.

The disclosed compounds and methods for preparing said compounds and articles of manufacture made therefrom include at least the following aspects:

Aspect 1: A compound of a general structure (I):

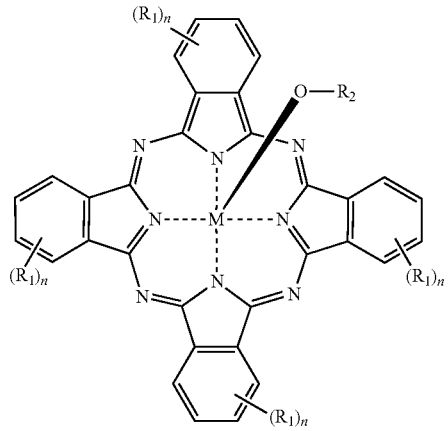

wherein M comprises aluminum, gallium, indium, or a combination thereof;

wherein "n" is an integer equal to or greater than 0;

wherein each $R_1$ can independently comprise a straight chain alkyl group, a branched alkyl group, a cycloalkyl group, an alkenyl group, an alkynyl group, an alkoxy group, an aryloxy group, heterocyclic group, a monocyclic aromatic group, a polycyclic aromatic group, an aryl group, an alkylaryl group, an arylalkyl group, an alkylene group, a hydrogen, a halogen, or a combination thereof;

wherein $R_2$ can comprise an optionally substituted aryl containing group comprising from greater than or equal to about 6 to about 22 carbon atoms, wherein the aryl containing group, if substituted, can be substituted at one or more positions with one or more of the same or different heteroatoms comprising a halogen, oxygen, sulfur, nitrogen, or a combination thereof.

Aspect 2: The compound of Aspect 1, wherein n ranges from about 0 to about 4.

Aspect 3: The compound of Aspect 1, wherein $R_2$ comprises an optionally substituted aryl containing group comprising from greater than or equal to about 6 to about 18 carbon atoms, wherein if substituted, can be substituted at one or more positions with one or more of the same of different heteroatoms.

Aspect 4: The compound of Aspect 1, wherein $R_2$ does not comprise a metal.

Aspect 5: The compound of Aspect 1, wherein $R_2$ does not comprise a heteroatom as a bridging group.

Aspect 6: The compound of Aspect 1, wherein $R_2$ comprises a halogen comprising fluorine, chlorine, bromine, iodine, or a combination thereof.

Aspect 7: The compound of Aspect 6, wherein $R_2$ does not comprise chlorine.

Aspect 8: The compound of Aspect 6, wherein $R_2$ comprises chlorine, and wherein the aryl containing group, if substituted, cannot be substituted at a para-position.

Aspect 9: The compound of Aspect 6, wherein $R_2$ comprises chlorine, and wherein the aryl containing group, if substituted, is substituted at one or more ortho-positions.

Aspect 10: A method for preparing a compound of the general molecular structure (I) comprising the steps of, a) providing a compound comprising a halogen-metal bond containing $R_1$ substituted phthalocyanines precursor, wherein the halogen comprises chlorine, bromine, iodine, fluorine, or a combination thereof, and wherein each $R_1$ independently comprises a straight chain alkyl group, a branched alkyl group, a cycloalkyl group, an alkenyl group, an alkynyl group, an alkoxy group, an aryloxy group, heterocyclic group, a monocyclic aromatic group, a polycyclic aromatic group, an aryl group, an alkylaryl group, an arylalkyl group, an alkylene group, a hydrogen, a halogen, or a combination thereof;
b) providing a reactant comprising an optionally substituted aryl (—$R_2$) and/or optionally substituted arylalcohol group (OH—$R_2$), wherein $R_2$ comprises from greater than or equal to about 6 to about 22 carbon atoms.
c) reacting the compound comprising a halogen-metal bond containing phthalocyanines precursor and the reactant in the presence of an organic solvent under conditions effective to form the compound of the general molecular structure (I), wherein the compound of the general molecular structure (I) is non-soluble, negligibly soluble, partially soluble in an organic solvent, or at least partially soluble in an organic solvent.

Aspect 11: The method of Aspect 10, wherein the reactant comprises an optionally substituted aryl (—$R_2$) or optionally substituted arylalcohol group (OH—$R_2$), wherein $R_2$ comprises from greater than or equal to about 6 to about 18 carbon atoms.

Aspect 12: The method of Aspect 10, wherein the organic solvent comprises toluene, dimethylsulfoxide, dichloromethane.

Aspect 13: A photovoltaic cell comprising a compound having the general molecular structure (I)

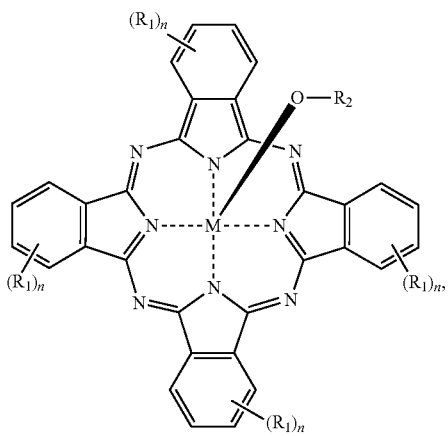

wherein M comprises aluminum, gallium, indium, or a combination thereof;
wherein "n" is an integer equal to or greater than 0;
wherein each $R_1$ can independently comprise a straight chain alkyl group, a branched alkyl group, a cycloalkyl group, an alkenyl group, an alkynyl group, an alkoxy group, an aryloxy group, heterocyclic group, a monocyclic aromatic group, a polycyclic aromatic group, an aryl group, an alkylaryl group, an arylalkyl group, an alkylene group, a hydrogen, a halogen, or a combination thereof; wherein $R_2$ can comprise an optionally substituted aryl containing group comprising from greater than or equal to about 6 to about 22 carbon atoms, wherein the aryl containing group, if substituted, can be substituted at one or more positions with one or more of the same or different heteroatoms comprising a halogen, oxygen, sulfur, nitrogen, or a combination thereof.

It is to be understood that the aspects described herein are not limited to the specific compositions, articles, devices, systems, and/or methods disclosed unless otherwise specified, as such can, of course, vary. It is also to be understood that the terminology used herein is for the purpose of describing particular aspects only and is not intended to be limiting.

The description of the invention is also provided as an enabling teaching of the invention in its best, currently known embodiment. To this end, those of ordinary skill in the relevant art will recognize and appreciate that changes and modification can be made to the various aspects of the invention described herein, while still obtaining the beneficial results of the present invention. It will also be apparent that some of the desired benefits of the present invention can be obtained by selection some of the features of the present invention without utilizing other features. Accordingly, those of ordinary skill in the relevant art will recognize that many modification and adaptations of the present invention are possible and can even be desirable in certain circumstances and are thus also a part of the present invention. Thus, the following description is provided as illustrative of the principles of the present invention and not in limitation thereof.

Various combinations of elements of this disclosure are encompassed by this invention, e.g. combinations of elements from dependent claims that depend upon the same independent claim.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

All publications mentioned herein are incorporated herein by reference to disclose and describe the methods and/or materials in connection with which the publications are cited.

It is also to be understood that the terminology used herein is for the purpose of describing particular aspects only and is not intended to be limiting. As used in the specification and in the claims, the term "comprising" can include the aspects "consisting of" and "consisting essentially of." Unless defined otherwise, all technical and scientific terms used herein have the same meaning as commonly understood by one of ordinary skill in the art to which this invention belongs. In this specification and in the claims which follow, reference will be made to a number of terms which shall be defined herein.

As used in the specification and the appended claims, the singular forms "a," "an" and "the" include plural referents unless the context clearly dictates otherwise. Thus, for example, reference to "an aromatic compound" includes mixtures of two or more such aromatic compounds. Furthermore, for example, reference to a filler includes mixtures of fillers.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Disclosed are materials, compounds, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of R groups are discussed, each and every combination and permutation of the inhibitor and the modifications to its R group that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C—F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

In this specification and in the claims which follow, reference will be made to a number of terms which shall be defined to have the following meanings:

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or cannot be substituted and that the description includes both unsubstituted lower alkyl and lower alkyl where there is substitution.

As used herein, the term or phrase "effective," "effective amount," or "conditions effective to" refers to such amount or condition that is capable of performing the function or property for which an effective amount is expressed. As will be pointed out below, the exact amount or particular condition required can vary from one aspect to another, depending on recognized variables such as the materials employed and the processing conditions observed. Thus, it is not always possible to specify an exact "effective amount" or "condition effective to." However, it should be understood that an appropriate effective amount will be readily determined by one of ordinary skill in the art using only routine experimentation.

A weight percent of a component, unless specifically stated to the contrary, is based on the total weight of the general molecular structure or composition in which the component is included. For example if a particular element or component in a composition or article is said to have 8% weight, it is understood that this percentage is relation to a total compositional percentage of 100%.

Compounds are described using standard nomenclature. For example, any position not substituted by any indicated group is understood to have its valence filled by a bond as indicated, or a hydrogen atom. A dash ("-") that is not between two letters or symbols is used to indicate a point of attachment for a substituent. For example, —CHO is attached through carbon of the carbonyl group. Unless defined otherwise, technical and scientific terms used herein have the same meaning as is commonly understood by one of skill in the art to which this invention belongs.

The term "Pc" as used herein is intended to refer to a phthalocyanine moiety, unless specifically stated to the contrary, and such a phthalocyanine moiety can comprise any phthalocyanine moiety, derivative or analogue thereof.

The term "alkyl group" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is an alkyl group containing from one to six carbon atoms.

The term "alkoxy" as used herein is an alkyl group bound through a single, terminal ether linkage; that is, an "alkoxy" group can be defined as —OR where R is alkyl as defined above. A "lower alkoxy" group is an alkoxy group containing from one to six carbon atoms.

The term "alkenyl group" as used herein is a hydrocarbon group of from 2 to 24 carbon atoms and structural formula containing at least one carbon-carbon double bond. Asymmetric structures such as (AB)C=C(CD) are intended to include both the E and Z isomers. This can be presumed in structural formulae herein wherein an asymmetric alkene is present, or it can be explicitly indicated by the bond symbol C.

The term "alkynyl group" as used herein is a hydrocarbon group of 2 to 24 carbon atoms and a structural formula containing at least one carbon-carbon triple bond.

The term "aryl group" as used herein is any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "cycloalkyl group" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulfur, or phosphorus.

The term "aralkyl" as used herein is an aryl group having an alkyl, alkynyl, or alkenyl group as defined above attached to the aromatic group. An example of an aralkyl group is a benzyl group.

The term "hydroxyalkyl group" as used herein is an alkyl, alkenyl, alkynyl, aryl, aralkyl, cycloalkyl, halogenated alkyl, or heterocycloalkyl group described above that has at least one hydrogen atom substituted with a hydroxyl group.

The term "alkoxyalkyl group" is defined as an alkyl, alkenyl, alkynyl, aryl, aralkyl, cycloalkyl, halogenated alkyl, or heterocycloalkyl group described above that has at least one hydrogen atom substituted with an alkoxy group described above.

The compounds disclosed herein can, independently, possess two or more of the groups listed above. For example, if $R_1$ is a straight chain alkyl group, one of the hydrogen atoms of the alkyl group can be substituted with a hydroxyl group, an alkoxy group, etc. Depending upon the groups that are selected, a first group can be incorporated within second group or, alternatively, the first group can be pendant (i.e., attached) to the second group. For example, with the phrase "an alkyl group comprising an ester group," the ester group can be incorporated within the backbone of the alkyl group. Alternatively, the ester can be attached to the backbone of the alkyl group. The nature of the group(s) that is (are) selected will determine if the first group is embedded or attached to the second group.

EXAMPLES

The following examples are put forth so as to provide those of ordinary skill in the art with a complete disclosure and description of how the compounds, compositions, articles, devices, and/or methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

In a first example, metal-phthalocyanines (Pcs) functionalized with m-cresol, as model phenoxy groups, can be successfully synthesized (Scheme 1). All Pcs were characterized by UV-Vis spectroscopy and cyclic voltammetry.

Scheme 1

Scheme 1: Phthalocyanines functionalized with m-cresol: (m-cresol)-AlPc, (m-cresol)-GaPc and (m-cresol)-InPc.

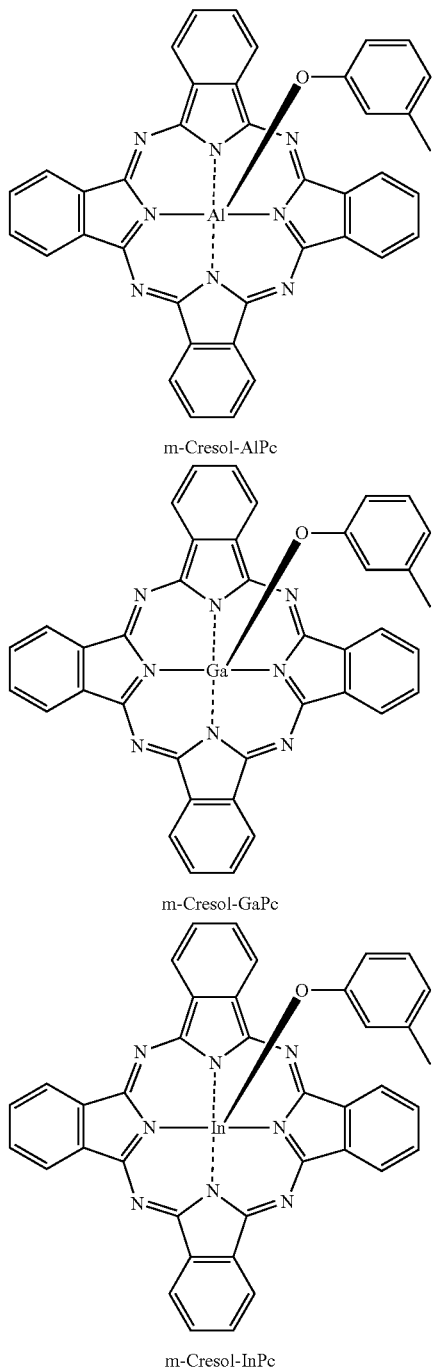

m-Cresol-AlPc m-Cresol-GaPc m-Cresol-InPc

Various methods to prepare the phthalocyanines (Pc) described herein can be used. The previous methodology of engineering the solid state arrangement of subphthalocyanines (*Ind. Eng. Chem. Res.* 2011, 50, 10910) can be extended to the synthesis of phthalocyanines (Pc) containing metals, as described herein. The chloride-metal bond of the group III metal containing Pc (MPcs) precursor is amenable to the displacement of the chloride ion with a nucleophile like a phenoxide group.

Prophetic Example

For example a mixture of Cl—AlPc (0.50 g, 0.87 mmol) and m-cresol (3.20 g, 29.63 mmol) could be added to 25 mL of Toluene in an oven dried and degassed 100 ml glass reactor. The reaction mixture could be heated to 115° C. overnight under ultra-pure $N_2$ gas. The crude product will be cooled to room temperature prior to being washed by basic aqueous solution (2M KOH) to remove excess phenol and dried under vacuum. In some cases the functionalized Pc can be washed with isopropanol (optionally ultrasonicated) and filtered to remove excess phenol. The resulting product will be characterized by $^1$H NMR spectroscopy (DMSO) and DART mass spectroscopy. Using similar conditions, m-cresol derivatives of AlPc, GaPc, InPc, (Scheme 1) could be synthesized in chlorobenzene and toluene.

Cyclic Voltammetry of Group III Metal Containing Phthalocyanines (Pcs):

Cyclic voltammetry (CV) was performed using a three-electrode cell assembly at room temperature in a 0.1 M tetrabutylammonium perchlorate (TBAP) in dichloromethane electrolyte solution. The working electrode was a glassy carbon disk electrode, the counter electrode was a polished platinum wire and the reference electrode was Ag/AgCl. An internal standard of bis(pentamethylcyclopentadienyl)iron ($E_{1/2,red}$=0.012 V) and a scan rate was 100 mV/s was used for all measurements. The samples were bubbled using nitrogen until no dissolved oxygen was present (20-30 minutes prior to each run). The characteristic cyclic voltammegrams for each group III metal containing Pcs can be found in FIG. 1. The results from the CV measurements can also be found in Table 1, as reported in terms of the peak oxidations ($E_{Peak}^{ox}$), the peak reductions ($E_{Peak}^{red}$) the half peak oxidation ($E_{1/2}^{ox}$) and the half peak reduction $E_{1/2}^{red}$). Finally as a comparison all the highest occupied molecular orbitals ($E_{HOMO}$s) corresponding to the group III metal containing Pcs were calculated from a reported empirical relationship $E_{HOMO}$=−(1.4±0.1)×($E_{1/2}^{ox}$)−(4.6±0.08) eV (Dandrade et al. *Organic Electronics* 2005, 6, 11-20)) and are reported in Table 1.

Both m-cresol-GaPc and m-cresol-InPc revealed single, reversible oxidations and two distinct reversible reductions corresponding to a HOMO level of −6.0 eV and −5.4 eV, respectively (FIG. 1, Table 1). The unreacted Cl—GaPc does not affect these electrochemical measurements, as it is not soluble in dichloromethane (DCM) and/or is present in small amounts.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

The invention claimed is:

1. A compound of a general structure (I):

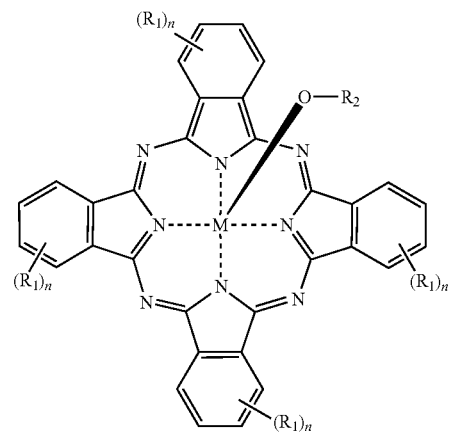

wherein M is aluminum, gallium, indium, or a combination thereof;

wherein "n" is an integer equal to or greater than 0;

wherein each $R_1$ independently is a straight chain alkyl group, a branched alkyl group, a cycloalkyl group, an alkenyl group, an alkynyl group, an alkoxy group, an aryloxy group, heterocyclic group, a monocyclic aromatic group, a polycyclic aromatic group, an aryl group, an alkylaryl group, an arylalkyl group, an akylene group, a hydrogen, a halogen, or a combination thereof;

wherein $R_2$ is a substituted aralkyl containing group having from about 7 to about 22 carbon atoms.

2. The compound of claim 1, wherein n ranges from about 0 to about 4.

3. The compound of claim 1, wherein the aralkyl containing group has 7 carbon atoms.

TABLE 1

Electrochemical and optical characterization of group III metal containing phthalocyanines.

| Sample ID | $E_{Peak}^{ox}$ (mV) | $E_{Peak}^{red}$ (mV) | $E_{1/2}^{ox}$ (mV) | $E_{1/2}^{red}$ (mV) | $E_{HOMO}$[1] (eV) | $E_{Gap,Opt}$[2] (eV) | $E_{LUMO}$[3] (eV) | $\lambda_{MAX}$ (nm) |
|---|---|---|---|---|---|---|---|---|
| mCresol-AlPc | — | −805 | — | −945 | — | 1.7 | — | 686 |
| mCresol-GaPc | 946 | −563, −950 | 1014 | −620, −991 | −6.0 | 1.7 | −4.3 | 687 |
| mCresol-InPc | 617 | −680, −894 | 598 | −722, −935 | −5.4 | 1.7 | −3.7 | 688 |

[1] $E_{HOMO}$ = −(1.4 ± 0.1) · ($E_{1/2}^{ox}$) − (4.6 ± 0.08) eV (Dandrade et al. *Organic Electronics* 2005, 6, 11-20)

[2] $E_{Gap,Opt}$ was determined using $E_{Gap,Opt}$ = h*C/λ, where h is planks constant, C is the speed of light and λ is the cut off wavelength of the absorbance spectra.

[3] $E_{LUMO}$ = $E_{HOMO}$ − $E_{Gap,Opt}$

4. The compound of claim 1, wherein the substituted aralkyl containing group does not comprise a metal.

5. The compound of claim 1, wherein the substituted aralkyl containing group does not comprise a heteroatom as a bridging group.

6. The compound of claim 1, wherein the substituted aralkyl containing group comprises a halogen, wherein the halogen is selected from a group consisting of comprising fluorine, chlorine, bromine, iodine, or a and any combination thereof.

7. The compound of claim 6, wherein the halogen is not chlorine.

8. The compound of claim 6, wherein the halogen is chlorine, and wherein the aralkyl containing group is not substituted at a para-position.

9. The compound of claim 1, wherein the substituted aralkyl containing group has chlorine at one or more ortho-positions.

10. A method for preparing a compound of the general molecular structure (I) as claimed in claim 1 comprising the steps of:
   a) providing a compound comprising a halogen-metal bond containing $R_1$ substituted phthalocyanines precursor, wherein the halogen is chlorine, bromine, iodine, fluorine, or a combination thereof, and wherein each $R_1$ independently is a straight chain alkyl group, a branched alkyl group, a cycloalkyl group, an alkenyl group, an alkynyl group, an alkoxy group, an aryloxy group, heterocyclic group, a monocyclic aromatic group, a polycyclic aromatic group, an aryl group, an alkylaryl group, an arylalkyl group, an akylene group, a hydrogen, a halogen, or a combination thereof;
   b) providing a reactant comprising a substituted arylalcohol group (OH—$R_2$), wherein $R_2$ has from 7 to about 22 carbon atoms;
   c) reacting the compound comprising a halogen-metal bond containing phthalocyanines precursor and the reactant in the presence of an organic solvent under conditions effective to form the compound of the general molecular structure (I) as claimed in claim 1, wherein the compound of the general molecular structure (I) is non-soluble, negligibly soluble, partially soluble in an organic solvent, or at least partially soluble in an organic solvent.

11. The method of claim 10, wherein the reactant $R_2$ has 7 carbon atoms.

12. The method of claim 10, wherein the organic solvent comprises toluene, dimethylsulfoxide, or dichloromethane.

13. A photovoltaic cell comprising a compound having the general molecular structure (I) as claimed in claim 1.

14. A photovoltaic cell comprising a compound having the general molecular structure of:

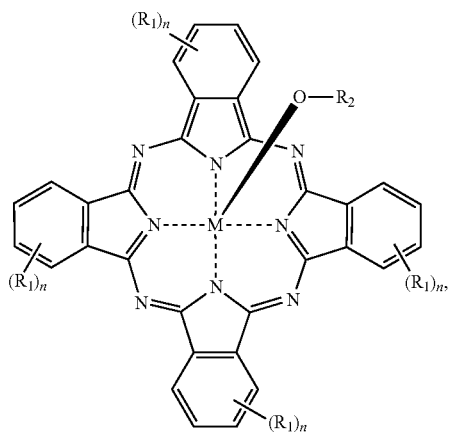

wherein M is gallium;

wherein "n" is an integer equal to or greater than 0;

wherein each $R_1$ independently is a straight chain alkyl group, a branched alkyl group, a cycloalkyl group, an alkenyl group, an alkynyl group, an alkoxy group, an aryloxy group, heterocyclic group, a monocyclic aromatic group, a polycyclic aromatic group, an aryl group, an alkylaryl group, an arylalkyl group, an akylene group, a hydrogen, a halogen, or a combination thereof;

wherein $R_2$ is an aryl containing group having from greater than or equal to about 6 to about 22 carbon atoms.

15. The photovoltaic cell of claim 14, wherein n is 1, $R_1$ is hydrogen, and $R_2$ is a 3-methyl aryl containing group.

16. The photovoltaic cell of claim 14, wherein n is 1, $R_1$ is hydrogen, and $R_2$ is a 3-methyl aryl containing group.

17. The compound of claim 1, wherein $R_2$ is further substituted at one or more positions with one or more of the same or different heteroatoms, wherein the heteroatom is selected from a group consisting of a halogen, oxygen, sulfur, nitrogen, and any combination thereof.

18. The compound of claim 1, wherein the aralkyl containing group is substituted at the meta position with a methyl group.

19. The compound of claim 1, wherein n is 1, $R_1$ is a hydrogen, and $R_2$ is a 3-methyl aryl containing group.

20. The compound of claim 1, wherein n is 1, $R_1$ is a hydrogen, and $R_2$ is a 3-methyl, and is substituted at one or more positions with one or more of the same of different heteroatoms, wherein the heteroatom is selected from a group consisting of a halogen, oxygen, sulfur, nitrogen, and any combination thereof.

\* \* \* \* \*

UNITED STATES PATENT AND TRADEMARK OFFICE
CERTIFICATE OF CORRECTION

PATENT NO. : 8,933,238 B2
APPLICATION NO. : 14/197799
DATED : January 13, 2015
INVENTOR(S) : Timothy P. Bender et al.

Page 1 of 1

It is certified that error appears in the above-identified patent and that said Letters Patent is hereby corrected as shown below:

In the Claims,

In claim 6, on column 23, line 8, delete "comprising".

In claim 6, on column 23, line 9, delete "or a".

Signed and Sealed this
Ninth Day of June, 2015

Michelle K. Lee
*Director of the United States Patent and Trademark Office*